United States Patent [19]
Annis et al.

[11] Patent Number: 4,819,256
[45] Date of Patent: Apr. 4, 1989

[54] RADIOGRAPHIC SENSITIVITY FOR DETECTION OF FLAWS AND CRACKS

[75] Inventors: Martin Annis, Cambridge; Paul Bjorkholm, Sharon, both of Mass.

[73] Assignee: American Science and Engineering, Inc., Cambridge, Mass.

[21] Appl. No.: 40,019

[22] Filed: Apr. 20, 1987

[51] Int. Cl.⁴ ......................................... G01N 23/201
[52] U.S. Cl. ....................................... 378/87; 378/58; 378/44; 250/302
[58] Field of Search ..................... 378/44, 45, 58, 90, 378/89, 86, 87, 88, 46; 250/302

[56] References Cited

U.S. PATENT DOCUMENTS

| Re. 28,544 | 9/1975 | Stein et al. | 378/58 |
| 3,197,638 | 7/1965 | Sinclair | 250/83.3 |
| 3,351,760 | 11/1967 | Brown | 250/106 |
| 3,704,370 | 11/1972 | Shelton | 250/65 R |
| 3,965,353 | 6/1976 | Macovski | 250/336 |
| 3,974,386 | 8/1976 | Mistretta et al. | 250/402 |
| 4,172,224 | 10/1979 | Lapinski et al. | 250/302 |
| 4,178,513 | 12/1979 | Dubois | 250/491 |
| 4,227,081 | 10/1980 | Caputo et al. | 250/321 |
| 4,323,973 | 4/1982 | Greenfield | 364/515 |
| 4,355,331 | 10/1982 | Georges et al. | 358/111 |
| 4,400,618 | 8/1983 | Bupp et al. | 250/302 |
| 4,577,337 | 3/1986 | Light | 378/044 |
| 4,591,478 | 5/1986 | Cohen et al. | 376/253 |
| 4,618,928 | 10/1986 | Honda et al. | 364/414 |
| 4,621,193 | 11/1986 | Van Hoye | 250/302 |
| 4,686,694 | 8/1987 | Berry et al. | 378/120 |

OTHER PUBLICATIONS

Stein et al., "Flying Spot X-Ray Imaging Systems", Materials Evaluation, vol. 30, No. 7, Jul. 1972, p. 137 et seq.

Primary Examiner—Carolyn E. Fields
Assistant Examiner—Joseph A. Hynds
Attorney, Agent, or Firm—Pollock, Vande Sande & Priddy

[57] ABSTRACT

A method of imaging for enhancing detection of cracks or flaws in an object using penetrating radiation is disclosed wherein a contrast medium is applied to an object before illumination and scatter radiation is detected from the object. This is achieved by employing a flying spot scanner and a backscatter imaging technique allowing imaging of objects which are not completely accessible, e.g. imaging the object where only one side accessible.

8 Claims, 5 Drawing Sheets

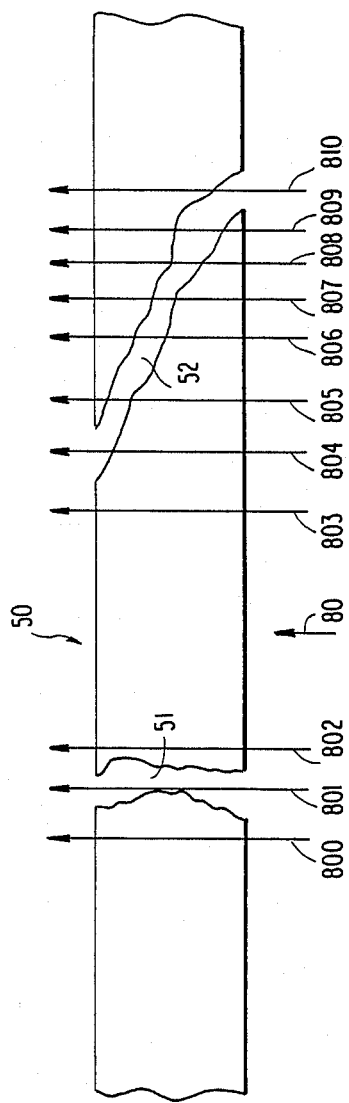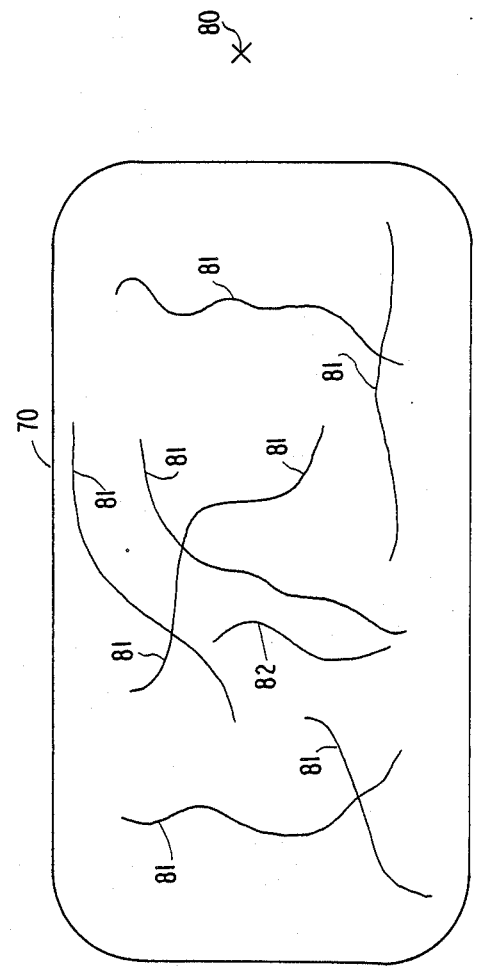
FIG.3
FIG.4

RADIOGRAPHIC SENSITIVITY FOR DETECTION OF FLAWS AND CRACKS

DESCRIPTION

1. Technical Field

The present invention relates to improvements in imaging using penetrating radiant energy and more particularly improvements for enhancing the detection of flaws or cracks.

2. Related Application

Reference is made to our copending application Ser. No. 876,632 filed June 20, 1986, the disclosure of which is incorporated by this reference.

3. Background Art

Imaging using penetrating radiant energy is widely employed in non-destructive testing. One of the major uses for such imaging is the detection of cracks or flaws in an object.

One form of such imaging employs a protection radiograph or shadowgraph (akin to the typical medical x-ray). In such application, reliable detection of a crack or flaw depends on achieving sufficient contrast in the resulting image. Achievement of the necessary contrast in accordance with some prior art techniques can depend on the orientation of the crack or flaw and thus these techniques are unreliable. The projection radiograph essentially identifies the absorption or transmissivity of the object along various lines of sight between the source of the penetrating radiant energy and the plane of the film or detector. If the flaw is oriented such that closely adjacent lines of sight see significantly different amounts of absorption or transmissivity, then the flaw can or should be recognizable in the resulting image. On the other hand, if the flaw is oriented such that there is little or no change in the transmissivity or absorption of adjacent lines of sight, then there will be inadequate contrast with which to identify the crack or flaw.

One technique for enhancing detection of such cracks or flaws is described by Cohen et al in U.S. Pat. No. 4,591,478. the patentee describes a technique of introducing into or exposing the object to be imaged to a liquid which includes an element having a higher atomic number than the atomic number characterizing the object to be imaged. He explains that this enhances detection because the liquid will be received in a crack or flaw and provide sufficient contrast in the resulting image to identify the flaw. Also pertinent are Shelton U.S. Pat. No. 3,704,370; Lapinski U.S. Pat. No. 4,172,224 and Caputo U.S. Pat. No. 4,227,081.

Another type of imaging using penetrating radiant energy is described as scatter imaging, see for example Stein et al, "Flying Spot X-Ray Imaging Systems", appearing in *Materials Evaluation*, Vol. XXX, No. 7, July 1972 at pages 137–148. Scatter imaging is useful in applications were the object to be imaged is not completely accessible. The use of the flying spot scanning back scatter imaging technique described by Stein et al for crack or flaw detection is contraindicated in that the backscatter technique has the curious feature that it cannot differentiate lead from air very easily since neither lead nor air provides significant backscatter. Sensing backscatter for crack or flaw detection (as opposed to imaging) is described in U.S. Pat. No. 3,197,638. Light, in U.S. Pat. No. 4,577,337, describes x-ray fluorescence testing of laminate structures. In the Light patent, detection of delaminations and cracks in cloth and epoxy-catalyst laminates is implemented in the form of an x-ray fluorescent technique in which a viscous medium or penetrant containing one or more elements of high atomic number is uniformly applied to a surface of a cloth and epoxy-catalyst laminate. After an interval sufficient to allow the penetrant to penetrate, the test coating is removed and the laminate is tested for x-ray fluorescence. According to the patentee, delamination and cracking is indicated by significant x-ray fluorescence, the location and surface dimensions of the damage is determined by X-Y scanning, the severity of delamination and cracking is determined by quantifying the received fluorescence, the depth of damage is determined by comparing the fluorescence attenuation for the elements of high atomic number.

The Light disclosure is particularly limited in a number of respects. While fluorescence testing is useful, it does require a combination of sufficient energy in the illumination beam to produce fluorescence and selection of a penetrant or contrast agent having an element which will fluoresce by illumination of the selected illuminating energy. Because of the characteristics of fluorescence, the Light disclosure is not easily extended to detecting cracks of flaws in high atomic number objects. Light proposes a high atomic number penetrant for detecting cracks or flaws in low atomic number objects. The converse, using a low atomic number penetrant, is contraindicated since low atomic number penetrants which fluoresce, fluoresce at energy levels which would be inadequate to escape the object and hence would not be detectable.

It is therefore an object of the invention to provide a method of imaging for enhancing detection of cracks or flaws in an object using penetrating radiant energy which is not limited as is the prior art referred to. It is another object of the present invention to provide a system or method which relies on imaging, where the emitted energy can be either impinging photons which have been redirected by interaction with the physical object being illuminated (scatter) and/or fluorescence energy emitted by either the object being illuminated or a penetrant or contrast agent which has been added thereto in response to excitation by the illuminating energy.

SUMMARY OF THE INVENTION

The invention meets these and other objects by employing a flying spot scanner and a backscatter imaging technique. This allows imaging of objects which are not completely accessible, e.g. imaging the object where only one side is accessible. More particularly, the method of the invention includes:

(a) providing a beam of penetrating radiant energy and repeatedly sweeping said beam over a line in space, (b) supporting an object for illumination by said beam and providing relative motion between said object and said line in space, (c) providing a radiation detector responsive only to scattered energy from said object as a consequence of its illumination by said beam of penetrating radiant energy, (d) applying a contrast medium to said object prior to said illumination, said contrast medium selected as one with atomic number significantly different from an atomic number characterizing said object, and (e) using signals produced by said radiation detector to develop an image representing cracks or flaws within which said contrast medium has accumulated.

To enhance the production of an image in which cracks or flaws are readily detectable, a contrast medium or penetrant is applied to the object prior to its illumination. The contrast medium or penetrant is selected as one with an atomic number significantly different from an atomic number characterizing the object.

For example, if one were interested in locating a crack or a flaw in an object characterized by an element or elements of high atomic number, then the contrast medium would be one which is characterized by an element of low atomic number. The amount of energy backscattered from an object is a strong function of the atomic number. The crack or flaw in this high atomic number object may well be totally invisible in a projection radiograph and it may also be totally invisible in a scatter image. If we injected or infused a low atomic number oil into the crack it would appear with good contrast in a scatter image. The high atomic number object would contribute little or no signal to the scatter image whereas the penetrant or contrast medium would, on the other hand, provide significant scatter thus producing the desired contrast.

Alternatively, if we were interested in locating a crack or a flaw in a material characterized by a low atomic number element, then our penetrant or contrast medium would be characterized by a high atomic number. Introducing such an agent into the crack or flaw would also provide the desired contrast in the scattered image. In this case, however, the object itself (characterized by low atomic number) would be an efficient scattering source. The contrast medium, on the other hand (characterized by high atomic number), would be a poor scattering source and absorb x-rays that would otherwise be scattered and the combination would produce the desired contrast.

Our contrast medium or penetrant can be selected within a wide degree of latitude so long as it is characterized by an element of appropriate atomic number. Depending on the object to be imaged, the contrast medium or penetrant can be a liquid and it can be applied to the object by submersion or spraying. Typically, after application, excess material is wiped away, but that portion of the contrast medium or penetrant which has penetrated cracks or flaws will remain.

Depending on the particular object, iodinated oil (characterized by high atomic number) can be employed. Gaseous penetrants or contrast mediums can also be employed; one example is xenon.

BRIEF DESCRIPTION OF THE DRAWINGS

The present invention will now be described in further detail so as to enable those skilled in the art to practice the invention, in the following portions of this specification when taken in conjunction with the attached drawings in which like reference characters identify identical apparatus and in which:

FIG. 3 is a cross-section of an object illustrating different types of flaws, one which will be seen in a projection radiograph and one which will not;

FIG. 4 is an example of a typical projection radiograph of an object illustrating how material variations can obscure a flaw;

DETAILED DESCRIPTION OF PREFERRED EMBODIMENTS

Figure 1:
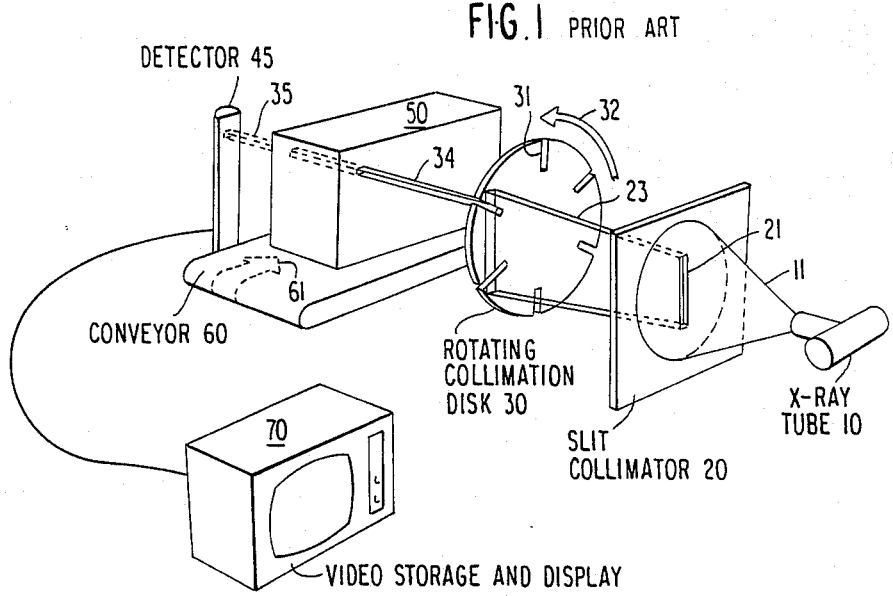
FIG. 1 illustrates the components of a prior art flying spot transmitted image scanner.
Figure 2:
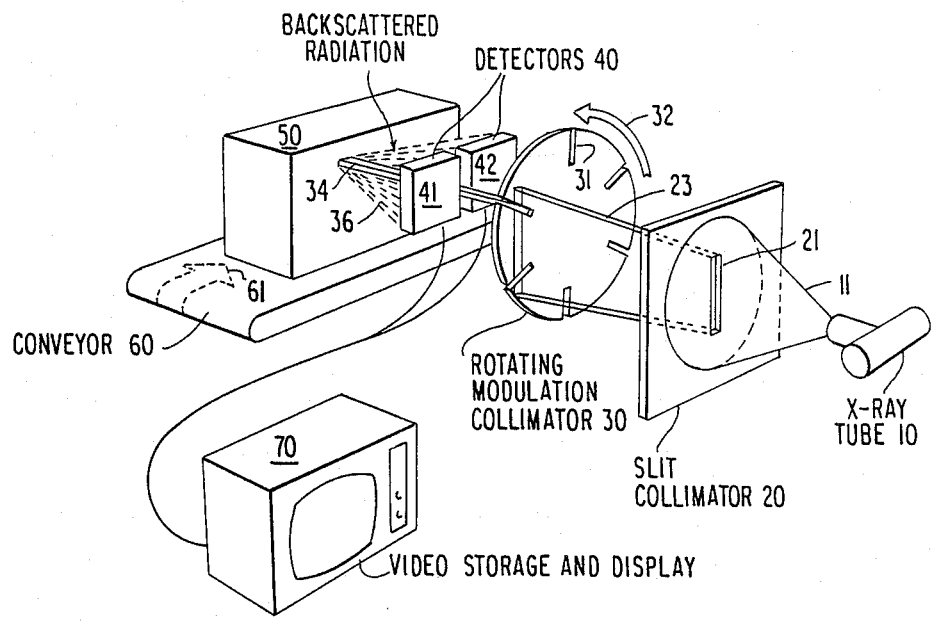
FIG. 2 illustrates the components of a prior art flying spot backscatter imaging scanner.

FIGS. 1 and 2 are schematic illustrations of prior art flying spot scanning imaging systems; FIG. 1 illustrates a transmitted or transmission image scanning system, whereas FIG. 2 showed a scattered or backscattered flying spot scanning imaging system. Both FIGS. 1 and 2 are reproduced from the Stein et al publication referenced above. In both FIGS. 1 and 2, an x-ray tube 10 (or other suitable source of penetrating radiant energy) emits a cone or fan-shaped beam 11 which impinges on a radiation opaque plate 20 having a slit 21 therein. As a result, a fan shaped beam 23 is emitted from the plate 20 and impinges on a rotating collimator 30. The collimator 30 has a plurality of slits 31, and as the plate 30 rotates in the direction 32, a pencil beam 34 is emitted from the collimation disk 30. As the disk 30 rotates, the pencil beam scans, and in FIGS. 1 and 2 that scanning action is vertically downward. Those skilled in the art will appreciate that the scanning motion of the pencil beam 34 can be reoriented within wide limits. As the pencil beam 34 scans, it illuminates the object 50. This illumination of the object 50 produces an attenuated pencil beam 35 (which is a theoretical extension of the pencil beam 34), e.g. it is a transmitted beam. At the same time, some of the penetrating radiant energy is backscattered, such as the radiation 36 shown in FIG. 2. In the case of FIG. 1, a detector 45 is arranged to intercept the transmitted, degraded pencil beam 35. The detector 45 converts the x-ray energy to electrical signals, in a manner well known to those skilled in the art, and those signals are used to drive a video storage and display apparatus 70. As the pencil beam 34 scans the object 50, the signals produced by the detector 45 represent the x-ray transmissivity of the object, or at least that portion of the object which is illuminated by the pencil beam 34. The video storage and display 70 produces an image of the x-ray transmissivity of that portion of the object. In order to develop an image of the x-ray transmissivity of the object 50, the object may be supported such as by the conveyor 60, and relative motion induced between the object 50 and the source 10, detector 45. One way of implementing that relative motion is to provide for motion of the conveyor 60 in the direction of the arrow 61. The detector 45 is arranged to lie along a line in space which is scanned by the pencil beam 34 as the collimating disk 30 rotates. The relative motion then is motion between the object 50 and the detector 45.

In the case of FIG. 2, the detector 45 is eliminated in favor of a backscatter detector 40 which comprises a pair of backscatter detector elements 41 and 42 placed on either side of the pencil beam 34. Because the scattered radiation can be scattered through a substantial angle, and to provide detection with as much efficiency as possible, the backscatter detectors preferably have a wide active area. For this purpose, the active area refers to the detector area in the plane through which photons cross the detector boundary. It is clear that (in sharp contrast to the active area of the scatter detector) the active area of the transmitted beam detector is determined by the pencil beam cross-section and the extent of the beam's sweep. Nevertheless, it is within the scope of the invention to use only a single backscatter detector, such as the detector 41 or 42. The active area of the backscatter detector is typically many times the active area of the transmission detector, such as the detector 45. In any event, the backscatter detector 40 produces a single signal which is input to the video storage and display apparatus 70 and used to develop an image of the object 50 which is illuminated by the scanning pencil beam 34. Whereas the image developed by the apparatus of FIG. 1 represents the x-ray transmissivity of the object 50, the image developed by the apparatus of FIG. 2 is based on the energy scattered by the object 50. This energy is a strong function of the atomic number (Z) of the object 50 or its components in that strong backscatter is developed by components of low atomic number (Z) and high atomic number components contribute little, if any, to such an image.

FIG. 3 is useful in explaining why in many cases prior art projection radiographs were not dependable as flaw detection instruments. FIG. 3 shows the cross-section of an object 50 including flaws 51 and 52 located therein. In the case of FIG. 3, both flaws are mass or structural defects, such as a crack. As shown in FIG. 3 the illuminating energy travels in the direction of the arrow 80. Since the projection radiograph represents the transmissivity of various lines of sight, and recognition of a flaw depends on recognizable contrast differences, it should be apparent that the flaw 51 may be readily recognized since adjacent lines of sight such as 800 and 801, on the one hand, and 801 and 802, on the other hand, will exhibit significant differences in transmissivity. On the other hand, typical lines of sight such as lines of sight 803–810 will represent little or no contrast relative to adjacent lines of sight. As a result, while the flaw 51 may well be readily detected, the flaw 52 will be invisible or near-invisible. Accordingly, the ability of the typical projection radiograph to detect a crack or flaw depends on part on the orientation of the crack or flaw. In general this makes the technique unreliable.

The preceding description has assumed that the object 50 is relatively uniform aside from the flaws 51 and 52. FIG. 4 on the other hand illustrates a typical projection radiograph of an object which includes a number of density and/or other material variations, such that the radiograph shows a number of such variations 81. FIG. 4 also shows a crack or a flaw 82 (or more accurately a representation of the crack or flaw) which appears on the projection radiograph. The problem represented in FIG. 4 is difficulty of separating the crack or flaw 82 from other material variations, such as the variations 81 which do not represent cracks or flaws. In general, the problems illustrated in FIGS. 3 and 4 call for some apparatus or technique to highlight or otherwise call attention to a crack or a flaw regardless of the orientation of the crack or flaw and regardless of other, inherent variations.

In accordance with a first embodiment of the invention, the apparatus of FIG. 2 is employed. Prior to imaging, the object has applied to it a contrast agent. The contrast agent is characterized, or has a component which is characterized, by an atomic number which is selected to sharply contrast with the atomic number which characterizes the object to be imaged. The contrast agent may be in gas or liquid phase depending on the type of crack or flaw to be detected and the characteristics of the object to be imaged.

Assume for example that we are imaging a steel plate; the steel plate is characterized by a high atomic number and therefore the contrast agent employed would be characterized by a low atomic number or at least have a component which is characterized by a low atomic number. As has already been explained in connection with FIG. 3, if the transmission image technique is employed, recognition of a crack or flaw may well depend on the orientation of the crack or flaw. If the backscatter imaging (of FIG. 2) is employed, it too may not reveal the crack or flaw. Both steel and the air which is assumed to occupy the crack or flaw 51 and 52 are poor scattering materials and therefore the scatter image would have little or no signal. If, prior to imaging, however, we apply an oil characterized by a low atomic number, such that, at the time of imaging the cracks or flaws 51, 52 were filled with the contrast medium, then that material would provide for a good scattering image. Accordingly, the backscattered image would provide good contrast between the flaws (represented by the scattering occasioned by the contrast medium) with respect to the surrounding steel which is a poor scattering material.

The invention is not limited to enhancing flaws in high atomic number materials. For example, assume that we were attempting to image flaws 51, 52 in a carbon composite. In that case, the contrast agent would be one which is characterized, or which has a component characterized, by a high atomic number. With a material characterized by a high atomic number residing in the cracks or flaws 51, 52, the resulting scatter image would highlight the cracks or flaws since while the object 50 being imaged is a good scattering material, the cracks or flaws would be poor scattering materials providing the desired contrast.

The apparatus of FIG. 2 can be employed in a second embodiment of the invention which is especially useful for imaging cracks or flaws in objects characterized by low atomic numbers. In this case, the contrast medium is selected as one which is or has a component providing a predetermined fluorescent radiation line in response to illuminating radiant energy of preselected energy levels. The quantum of fluorescent radiation seen from any object is a strong function of the atomic number of the material and the energy of the exciting radiation. In order for the fluorescent radiation to be detectable, it must have sufficient energy to escape the object within which it is generated. For this reason, contrast media represented or characterized by low atomic numbers are poor sources for fluorescent radiation since the fluorescent radiation they product typically has insufficient energy to escape the object and is therefore relatively undetectable. On the other hand, contrast media which are characterized by or have a component which is characterized by a high atomic number will be capable of emitting fluorescent radiation of sufficient energy to escape the object being illuminated. Two examples of such contrast media are iodinated oils and barium. A further gaseous contrast medium is xenon. When used as a contrast medium, all three are characterized by high atomic number. So long as the exciting energy, e.g. the pencil beam 34, has sufficient energy to produce fluorescence, the fluorescence produced by the contrast medium is capable of being detected by the detectors 40. Just as in the case of other radiation, fluorescent radiation comes off at a wide variety of angles and therefore use of a detector with a large active area is preferable. When relying on fluorescent radiation for crack or flaw enhancement, the energy level of the pencil beam 34 must be selected to be capable of exciting the fluorescence. The energy of the illuminating or incident photons must be above the K-absorption edge for the material of interest. For a typical x-ray (polychromatic) source, the peak voltage must be significantly higher than the K-absorption edge to ensure that many of the photons exceed the threshold value. Those photons below the K-edge are useless for fluorescence and might be filtered out of the illumination beam.

In this embodiment of the invention, the detector 40 must be tailored to ensure that the signals produced by the detector are related to the predetermined fluorescent radiation line which is expected to be emitted by the contrast agent to the exclusion of signals representing other scattered radiation. Once the predetermined fluorescent radiation line which will be used has been selected, those skilled in the art are aware of conventional techniques for tailoring the detector response so as to respond essentially only to the predetermined fluorescent radiation line to the exclusion of other, scattered radiation.

One suitable technique for tailoring the detector so that it responds to the predetermined fluorescent radiation line but does not respond to scattered radiation, is to employ two conventional detectors (scintillators) each preceded by a filter. Since each element is reasonably transparent to its own fluorescent radiation, one of the filters is made of the material of interest, see FIG. 8. The thickness of the filter F1 is adjusted to produce a significant difference in attenuation across the K-edge. Thus, element F1 will differentially filter out x-rays just above the K-edge. The second filter has a slightly higher Z material but a nearly identical transmission characteristic with its K-edge displaced to a higher energy. The difference between the energy observed in the two detectors will be proportional to the energy in a tight region around the fluorescent line of interest and in this way focus on the fluorescent radiation line to the exclusion of (almost all) scattered radiation.

Figure 8:
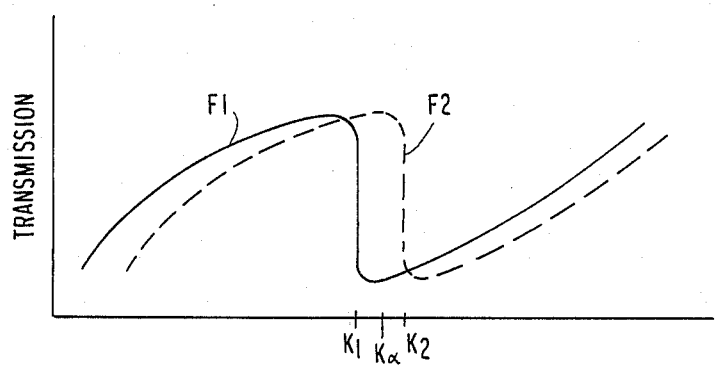
FIG. 8 illustrates the transmission characteristic of filters used to tailor the detector characteristic and FIG. 9 shows the overall characteristic of the two filters.
Figure 9:
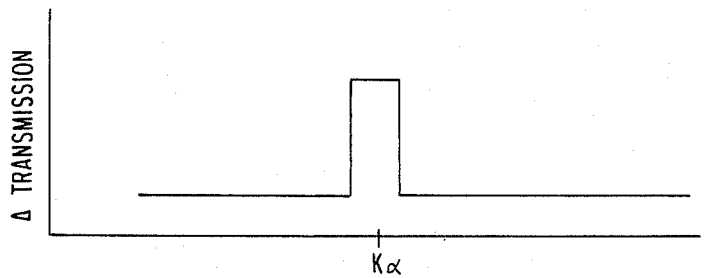
Figure 10:
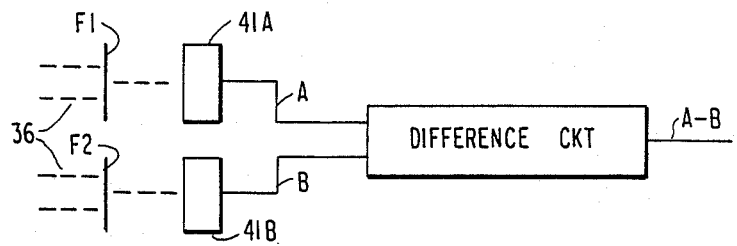
FIG. 10 shows the arrangement of filters, detectors and circuitry.

FIG. 10 shows an arrangement for tailoring the response of the detector 40 so that it responds substantially only to the predetermined fluorescent radiation line. FIG. 8 shows how the characteristic of the filters consisting of elements F1 and F2 restricts the response of the detector 41 to the predetermined fluorescent radiation line, the energy in the vicinity of $K_\alpha$. More particularly, FIG. 8 (labelled transmission), shows the transmission characteristics of the filter elements F1 and F2, respectively. The discontinuity in these transmission characteristics is a result of a particular K-edge. FIG. 8 also shows the location of the predetermined fluorescent radiation line $K_\alpha$. FIG. 9 shows, in the lower curve (labelled Δ transmission), the energy characteristic passing the detector arrangement of FIG. 10.

As shown in FIG. 9, the energy characteristic is relatively flat until an energy approximately equal to the K-edge discontinuity in the transmission characteristic of element F1. At this point, the composite transmission quickly rises, and it maintains this particular transmission characteristic as energy increases until an energy level is reached which is above $K_\alpha$, corresponding to the K-edge discontinuity in the characteristic of filter element F2. Above this energy level, the composite transmission characteristic is substantially the lower level exhibited for energies below the K-edge associated with the filter element F1. Since each element is reasonably transparent to its own fluorescent radiation, the filter F1 can comprise material identical to the targeted component. The second filter F2 comprises a material of higher Z and a nearly identical transmission characteristic except near the K-edge. Thus it should be apparent that by properly selecting the filters F1 and F2, the only energy reaching detector 41 will be in the region of $K_\alpha$, the preselected fluorescent radiation line.

FIG. 10 shows an arrangement for achieving the characteristic such as that shown in FIG. 9. As shown in FIG. 10, the detector 41 is split into two detector elements 41A and 41B, both located so as to detect the scattered energy 36. A first filter element F1 is located between a source of the predetermined fluorescent radiation line and the detector element 41A, and a different filter element F2 is located between a different detector element 41B and the source of the predetermined fluorescent radiation line. Each of these detectors develops a signal corresponding to the intensity of the energy impinging on the detector. The signal A produced from the element 41A reflects the energy passing the filter element F1 and the signal B reflects the energy passing the filter element F2. A difference circuit produces, at an output, the difference (A−B). It should be apparent to those skilled in the art that the arrangement of FIG. 10 produces an output signal (A−B) which, as a function of energy level, has the characteristic shown in FIG. 9. Thus, the output of (A−B) is the output of the detector 41. Of course a similar arrangement would be employed for other detectors (such as detector 42), if any. The two detector elements 41A and 41B are arranged symmetrically with respect to the scattered energy 36. If both detector elements 41 and 42 are arranged as in FIG. 10, then, for example, element 42A and 41B are located closer to the illuminating beam than elements 42B and 41A, respectively.

Figure 5:
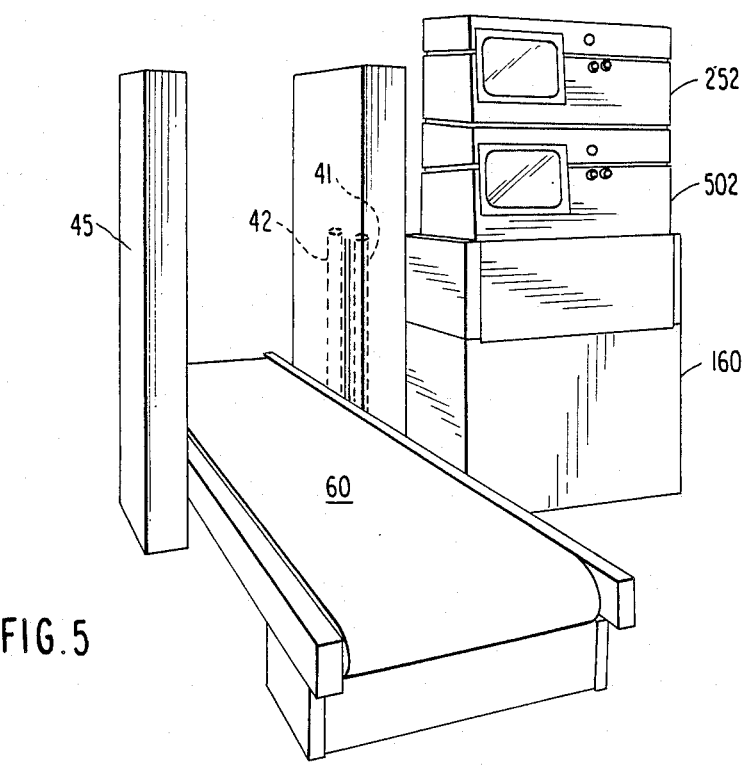
FIG. 5 illustrates the equipment employed with an embodiment of the invention which develops two different images.
Figure 6:
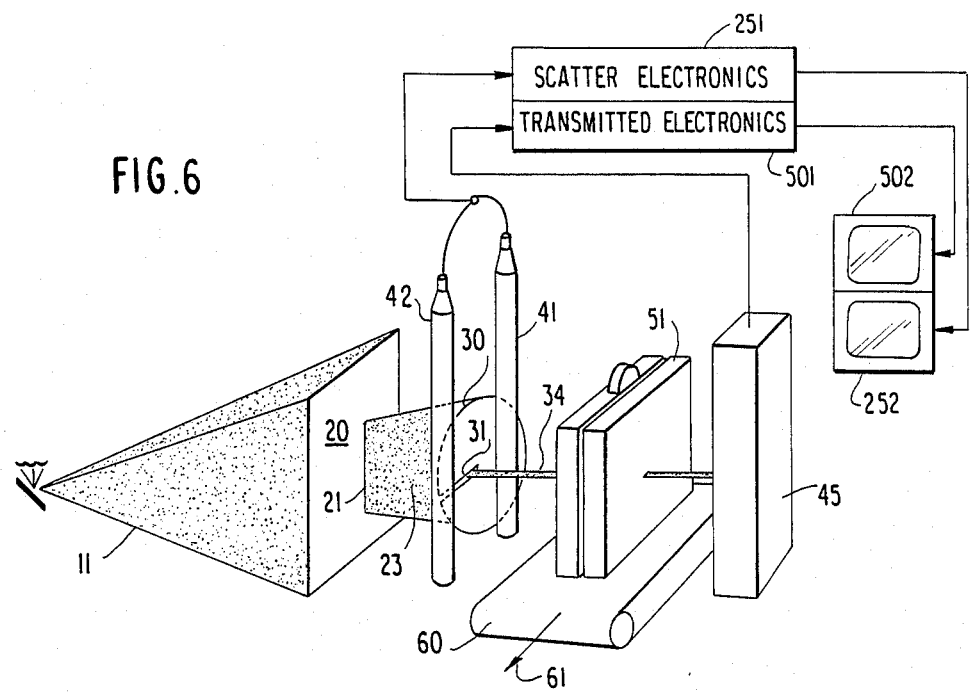
FIG. 6 is a schematic version of FIG. 5, illustrating the operation of the apparatus of FIG. 5 in more detail.

As described in our copending application Ser. No. 876,632 filed June 20, 1986 (the disclosure of which is incorporated by this reference) and assigned to the assignee of this application, it is sometimes useful in imaging to develop both transmission and scatter images. In another embodiment of this invention, two such images are employed. FIG. 5 shows the apparatus that can be employed. FIG. 5 shows an equipment cabinet 160 which can house the source of the flying pencil beam 34, e.g. the x-ray tube 10, slit collimator 20, rotating collimator 30. The flying pencil beam 34 is emitted from the cabinet 160 and scans in a plane located between the detectors 41 and 42 (shown dotted in FIG. 5). The transmission detector 45 is also shown in FIG. 5. Both the detectors 40 (scatter detectors) and 45 (transmit detector) generate the corresponding signals when an object is illuminated by the flying pencil beam 34. FIG. 6 represents, in schematic fashion, the apparatus represented in FIGS. 1, 2 and 5. The signals produced by the scatter detector 40 is input to the scatter electronics 251. The output of the scatter electronics 251 is input to a display 252 which therefore displays a scatter image of the object 51 which is illuminated by the flying pencil beam 34. On the other hand, the output of the detector 45 is input to the transmitted electronics 51, the output signal of which is provided to a display 502. As a result, the display 502 develops a transmission image of the object 51. In accordance with this embodiment of the invention, a suitable contrast agent is applied to the object 51 prior to imaging. The contrast agent, as described, may be either gaseous or liquid and suitably selected with an appropriate atomic number, to provide a desired effect. In the embodiment shown in FIG. 6, in order to provide contrast in both transmission and scatter images, the contrast agent can be selected with these two criteria in mind. A suitable contrast medium, for example for detecting flaws in low atomic number material would be an iodinated oil. The iodine component provides contrast in the transmission image and the oil based carrier supplies contrast in the scatter image.

FIGS. 5 and 6 also represent the equipment employed in still another embodiment of the invention. In this embodiment of the invention, the detectors 40 are tailored (as described with reference to FIGS. 8-10) to respond to a predetermined fluorescence radiation line and thus the detector 40, electronics 251 and display 252 provide a fluorescence image. For use in this embodiment of the invention, the x-ray tube 10 must provide x-rays of energy level sufficient to excite the predetermined fluorescence radiation line. In this embodiment of the invention, the iodine in the iodinated oil provides contrast in the fluorescence image as well as in the transmission image.

Figure 7:
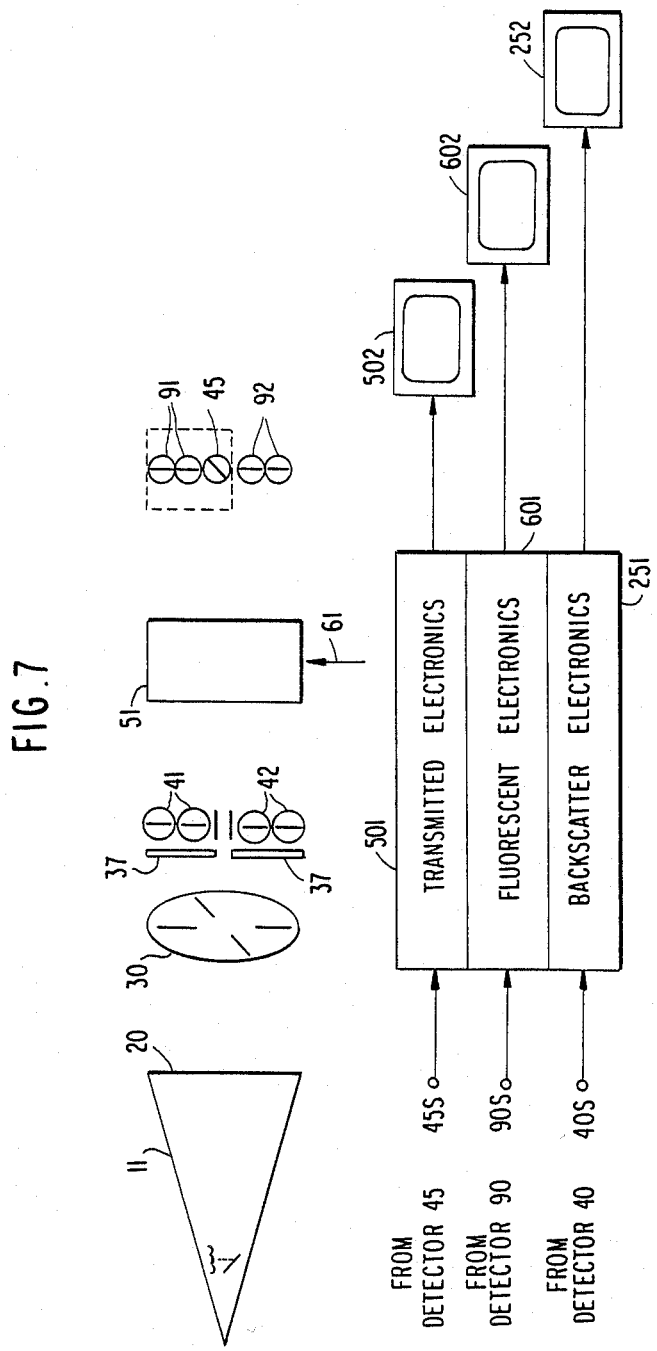
FIG. 7 is a schematic version of equipment used with a different embodiment of the invention, one in which three different images are developed.

FIG. 7 illustrates, in schematic fashion, equipment employed in still another embodiment of the invention. FIG. 7 differs from FIGS. 5 and 6 in that, in addition to the scatter detectors 41 and 42 and the transmission detector 45, there is an additional detector 90 comprising detector elements 91 and 92. The detector elements 91 and 92 have their characteristics tailored to respond substantially only to a predetermined fluorescent radiation line. The signals provided by the detector 90 are input to a fluorescent electronics element 601, the output of which drives the display 602. In this embodiment of the invention, three different images are developed, the display 502 develops a transmission image, the display 252 develops a backscatter image and the display 602 develops a fluorescent image. In connection with FIG. 7, the characteristics of the detector 90 are tailored to respond substantially only to the predetermined fluorescence radiation line and the energy level in the x-ray tube 10 is selected so as to excite this predetermined fluorescence radiation line either in the contrast medium or in the object being illuminated. If for example the contrast medium again is an iodinated oil, the iodine component provides contrast in transmission and fluorescence, the oil based carrier provides contrast in scatter.

In the preceding description of various embodiments of the invention, we have referred to the scatter detector as being of backscatter (that is, placed on the same side of the object being imaged as was the source). Those skilled in the art will appreciate that that is not at all essential to the invention, e.g. in every case the backscatter detector 40 can be replaced by a forward scatter detector, e.g. on the other side of the object being imaged than the source. Furthermore, although we have described the embodiment of FIGS. 5 and 6 as developing transmitted and scattered signals or transmitted and fluorescent signals, it is also within the scope of the invention to develop scatter and fluorescent images. A further variation on the embodiments shown in FIG. 7 is to develop fluorescent and forward scatter images as well as the transmitted image.

Note that the iodinated oil which is specifically mentioned as a contrast medium is only one example; such medium is particularly appearing because the human body tolerates iodine fairly well. Any high Z material works well. Originally, thorium was used and produced excellent images until its toxicity was fully realized. In general, any high atomic number contrast agent can be used so long as it meets two criteria: (1) its atomic number shows an atomic number difference ($\Delta Z$) between the atomic number of the contrast agent and the atomic number of the material being imaged which exceeds some threshold and (2) the contrast agent has physical characteristics allowing it to penetrate cracks, etc.

While several preferred embodiments of the invention have been described in detail, those skilled in the art after reviewing the description will understand that other and further variations of the invention fall within the spirit and scope of the invention which is to be construed in accordance with the attached claims.

We claim:

1. A method of imaging for enhancing detection of cracks or flaws in an object using penetrating radiant energy comprising the steps of:
   (a) providing a beam of penetrating radiant energy and repeatedly sweeping said beam over a line in space,
   supporting an object for illumination by said beam and providing relative motion between said object and said line in space,
   (c) providing a radiation detector responsive only to scattered energy from said object as a consequence of its illumination by said beam of penetrating radiant energy,
   (d) applying a contrast medium to said object prior to said illumination, said contrast medium selected as one with atomic number significantly different from an atomic number characterizing said object so as to provide contrast in a scatter image, and
   (e) using signals produced by said radiation detector to develop an image representing cracks or flaws within which said contrast medium has accumulated.

2. The method of claim 1 in which said radiation detector provided in said step (c) has an active area large in relation to a cross section of said beam.

3. The method of claim 7 in which said step of applying a contrast medium includes contacting said object, by wiping, immersing or spraying with a liquid contrast medium, and removing excess amounts of said medium.

4. The method of claim 3 in which said contrast medium is an iodinated oil.

5. The method of claim 1 or 7 in which said step of applying a contrast medium includes exposing said object to a gaseous contrast medium.

6. The method of claim 5 in which said gaseous medium is xenon.

7. The method of claim 1 which comprises the further steps of:
   (f) providing a second radiation detector responsive to energy transmitted, unchanged in direction, through said object, and (g) using signals produced by said second radiation detector to develop a second image representing a shadowgraph of said object.

8. The method of claim 7 which comprises the further steps of:

(h) providing a third radiation detector responsive substantially only to a predetermined fluorescence line from said contrast medium, (i) using signals produced by said third radiation detector to develop a third image representing a shadowgraph of said object, wherein (j) said step (a) includes selecting an energy level of said beam as sufficient to induce said predetermined fluorescence line from said contrast medium.

* * * * *